(12) United States Patent
Teal et al.

(10) Patent No.: US 8,647,615 B1
(45) Date of Patent: Feb. 11, 2014

(54) METHODS FOR ATTRACTING HONEY BEE PARASITIC MITES

(75) Inventors: Peter EA Teal, Gainesville, FL (US); Adrian J. Duehl, Gainesville, FL (US); Mark J. Carroll, Tucson, AZ (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 207 days.

(21) Appl. No.: 13/220,017

(22) Filed: Aug. 29, 2011

Related U.S. Application Data

(60) Provisional application No. 61/377,553, filed on Aug. 27, 2010.

(51) Int. Cl.
*A01N 35/08* (2006.01)
*A01N 35/00* (2006.01)

(52) U.S. Cl.
USPC .............................. 424/84; 424/409; 514/603

(58) Field of Classification Search
USPC .......................................... 424/409; 514/603
See application file for complete search history.

(56) References Cited

U.S. PATENT DOCUMENTS

| | | | |
|---|---|---|---|
| 6,543,181 B1 * | 4/2003 | Baker et al. ..................... | 43/107 |
| 2005/0090560 A1 * | 4/2005 | Erickson et al. .............. | 514/675 |

* cited by examiner

*Primary Examiner* — Anoop Singh
*Assistant Examiner* — Yanzhi Zhang
(74) *Attorney, Agent, or Firm* — John D. Fado; G. Byron Stover

(57) ABSTRACT

A method for attracting honey bee parasitic mites to an object or area, involving treating the object or area with a composition containing a honey bee parasitic mites attracting effective amount of at least one compound selected from butyric acid, isobutyric acid, or mixtures thereof, and optionally a carrier or carrier material.

3 Claims, 11 Drawing Sheets
(1 of 11 Drawing Sheet(s) Filed in Color)

METHODS FOR ATTRACTING HONEY BEE PARASITIC MITES

REFERENCE TO RELATED APPLICATION

This application claims the benefit of U.S. Provisional Application No. 61/377,553, filed 27 Aug. 2010, which is incorporated herein by reference in its entirety.

BACKGROUND OF THE INVENTION

The present invention relates to a method for attracting honey bee parasitic mites to an object or area, involving treating the object or area with a composition containing a honey bee parasitic mites attracting effective amount of at least one compound selected from butyric acid, isobutyric acid, or mixtures thereof, and optionally a carrier or carrier material.

*Varroa* mites are obligate parasites of honey bee (*Apis mellifera*) adults and brood. The mites feed throughout their life cycle on the hemolymph of bees (thus weakening bees), and the mites vector a large number of viruses. This interaction likely contributes significantly to colony collapse disorder (CCD), a major source of loss to apiculture operations. Adult female mites use adult bees as phoretic hosts to move around the colony, but must acquire a specific-age bee larva to successfully reproduce. During host acquisition (cell invasion), the female mite detects an appropriately aged larval host (an older fifth instar larva near capping) and moves off the phoretic host into the larval host cell. The mite is then capped (enclosed) in the cell with the bee larva by worker bees and reproduces while its host develops through pupation into an adult bee. Female mites manage to successfully locate an appropriate larval host in a complex hive environment filled with cues from similar but age-inappropriate younger bee larvae.

Every European honeybee colony in the United States, and in most other countries in the world, is infested with *Varroa* mites to some degree. The apiculture industry in the US accounts for more than $12 billion/year in pollination services alone. The *Varroa* mite is considered the most critical pest to honeybee health and consequently pollination services rendered by beekeepers. Migratory beekeepers assume that 30% of all hives will die during annual moves to pollinate crops across the US and consider the *Varroa* mite to be a significant cause of die off. The industry is desperate for new effective strategies to control the mite that do not require the use of pesticides, primarily because mites develop resistance rapidly and beekeepers realize that bees also suffer from the effects of miticides.

Reducing the mortality associated with the *Varroa* mite and increasing the health of honeybees by controlling this parasite will result in many millions of dollars in savings to beekeepers alone. Additionally, pollination services will be increased because the numbers of colonies available to pollinate will be increased and healthy bees are more effective in pollination than weakened bees. For example, honeybees are obligate pollinators for almonds and one of the limiting factors for almond production in California is the availability of bees to pollinate. Effectively controlling *Varroa* mite will therefore have significant impacts on crop production throughout the US and other countries.

Thus alternatives to chemical pesticides are needed.

Herein we describe two chemicals (butyric acid and isobutyric acid) that surprisingly act as attractants to phoretic *Varroa* mites.

SUMMARY OF THE INVENTION

In accordance with the present invention there is provided a method for attracting honey bee parasitic mites to an object or area, involving treating the object or area with a composition containing a honey bee parasitic mites attracting effective amount of at least one compound selected from the group consisting of butyric acid, isobutyric acid, and mixtures thereof, and optionally a carrier or carrier material.

BRIEF DESCRIPTION OF THE DRAWINGS

The patent or application file contains at least one drawing executed in color. Copies of this patent or patent application publication with color drawing(s) will by provided by the Office upon request and payment of the necessary fee.

DETAILED DESCRIPTION OF THE INVENTION

Figure 1:
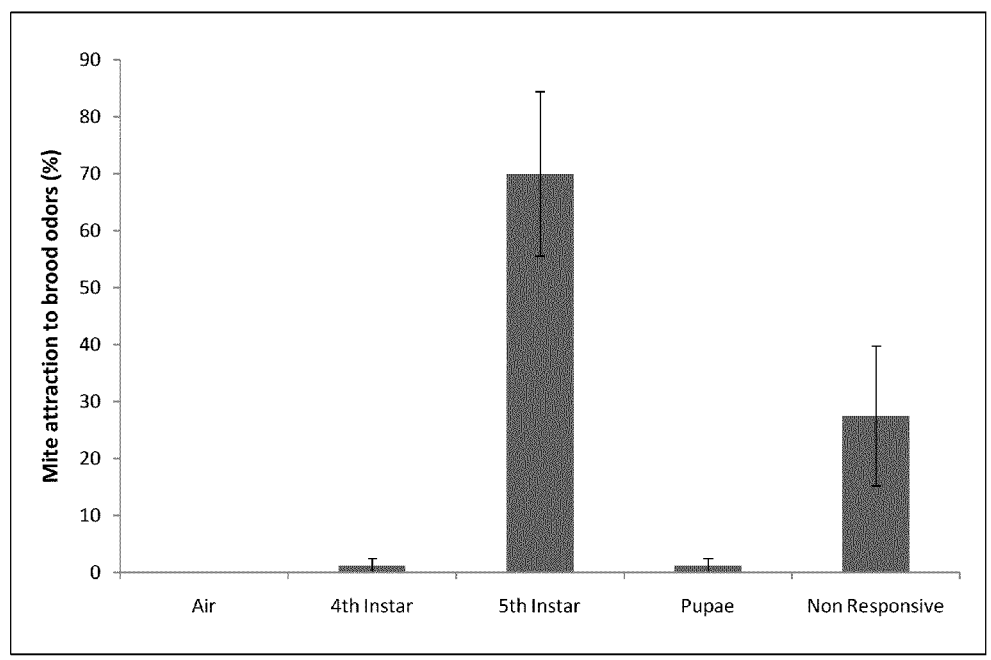
FIG. 1 shows attraction of *Varroa* mites to brood odors collected directly from living bee brood as described below; some mites did not leave their introduction pin and so were classified as non-responsive.

A method is disclosed for attracting honey bee parasitic mites to an object or area, involving treating (or exposing) the object (e.g., insect trap) or area (e.g., field, orchard) with a composition containing a honey bee parasitic mites attracting effective amount of at least one compound selected from the group consisting of butyric acid, isobutyric acid, and mixtures thereof, and optionally a carrier or carrier material. The carrier or carrier material may be, for example, agronomically or physiologically or pharmaceutically acceptable carriers or carrier materials. The carrier or carrier material as used herein is defined as not including the body of an insect (e.g., honey bees) or the extract from which a compound (e.g., butyric acid, isobutyric acid) is isolated.

The attractant of the present invention may be applied with a carrier component. The carrier component can be a liquid or a solid material. As is known in the art, the vehicle or carrier to be used refers to a substrate such as a membrane, hollow fiber, microcapsule, cigarette filter, gel, polymers, or the like. All of these substrates have been used to release insect attractants in general and are well known in the art.

The amount of attractant used will be at least an effective amount. The term "effective amount," as used herein, means the minimum amount of attractant needed to attract honey bee parasitic mites to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% of the honey bee parasitic mites and would be statistically significant in comparison to a control. The attractant composition may or may not contain a control agent for honey bee parasitic mites, such as a biological control agent or an insecticide known in the art to kill honey bee parasitic mites. Other compounds may be added to the attractant composition provided they do not substantially interfere with the intended activity of the attractant composition; whether or not a compound interferes with attractant activity can be determined, for example, by the procedure utilized below. Such other compounds may be present generally from about 0.0025% to about 20% in the composition.

The attractants could be used in pest management strategies: (1) as a component of an attracticide which combines it with a feeding stimulant and lethal doses of insecticide or pathogen. Such an attracticide would not only specifically target honey bee parasitic mites populations but would also result in an overall decrease in application rates for pesticides to crop ecosystems; (2) for monitoring populations of colonizing honey bee parasitic mites early in the season; (3) in deployment of the trap crop method of honey bee parasitic mites control; (4) to indicate honey bee parasitic mites movement within fields; or (5) in conjunction with antifeedants (Murray, K. D., et al., Entomol. Exp. Appl., 80: 503-510 (1996)) in "push-pull" strategies of insect management.

The term "honey bee" refers to members of the Order Hymeoptera, Family Apidae, and includes, by way of example, the species *Apis mellifera* and *Apis cerana*.

For the purposes of this invention, a compound is applied for its intended purpose at a level that is greater than the ambient background level. This is described further with reference to butyric acid, but applies to all embodiments of the invention. As discussed herein, butyric acid is produced by honey bees, and thus is naturally present in the ambient air of a colony, denoted hereinafter as the "background level." For the purposes of this invention, the effective amount of butyric acid to control mites is an amount greater than the ambient background level of butyric acid naturally present in the air at the time of exposure. That is, control of parasitic mites is carried out by exposing the target mites to a source of butyric acid other than or in addition to the naturally present background level. In one aspect of the invention, naturally occurring levels of butyric acid are augmented to ensure persistence of this volatile compound at attractant levels.

Unless defined otherwise, all technical and scientific terms used herein have the same meaning as commonly understood by one of ordinary skill in the art to which the invention belongs. The term "about" is defined as plus or minus ten percent. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Experiment 1

We first compared mite behavioral responses to host (late fifth instar bee larvae near capping) and non-host (all other life stages) volatiles in a choice bioassay. Specific age cohorts of bee brood ($4^{th}$ instar larvae, late $5^{th}$ instar larvae, and pupae 48 hours after capping) were obtained by confining the queen bee on an isolated patch of fresh empty cell comb for 6 hours. The queen filled the cells with eggs and was then excluded to prevent further oviposition. The frame of eggs was then placed in the center of the colony to ensure the even development of bee brood over time. We evaluated mite attraction and arrestant (stopping) responses to host volatiles directly infused into empty cells in an open comb choice arena.

Fresh brood volatiles were captured by enclosing a patch of brood (~90 per sample) under a glass petri dish embedded in the comb wax. Bee larvae and pupae were maintained at hive environmental conditions by gently pumping clean, charcoal-filtered, humidified (~70% relative humidity), warm (93° F.) air into the glass enclosure with a push-pull air flow system. To obtain odors from healthy, unstarved brood, all bee brood were used as odor sources within two hours of enclosure. Host volatiles from enclosed brood were relayed through Teflon tubing to the comb array by an ultralow (6 mL/hr) push-pull air flow system. Odors were directly infused into single empty cells on the comb array through a glass capillary tube. The tube extended approximately 3 mm (⅓× depth) into the center of the infused cell, and was held in place by a rigid clamp. Each of the four different odor sources (fourth instar larvae, fifth instar larvae, pupae, and air control) were presented on the open comb array in a 3×4 grid at three different points.

Phoretic female *Varroa* mites were removed from worker bees by brush and maintained at 30° C. at high humidity until use in the bioassay. To minimize disturbance, each female mite was transferred to the comb after crawling on to an insect pin. Each pin was then embedded in the comb at one of six release points. 40 mites were released on each comb array per trial. We examined the distribution of female *Varroa* mites relative to volatile-infused cells on the comb array thirty minutes after release on the array. Mites that were located in a volatile-infused cell or cells immediately adjacent to that cell were considered attracted to that odor treatment. All other mites that were not in proximity to the infused cells were treated as non-responders (NR) and were excluded from statistical analysis. Mites were surprisingly attracted to and remained in cells infused by host odors ($5^{th}$ instar) at higher rates than cells infused by non-host volatiles (FIG. 1).

Experiment 2

Figure 2:
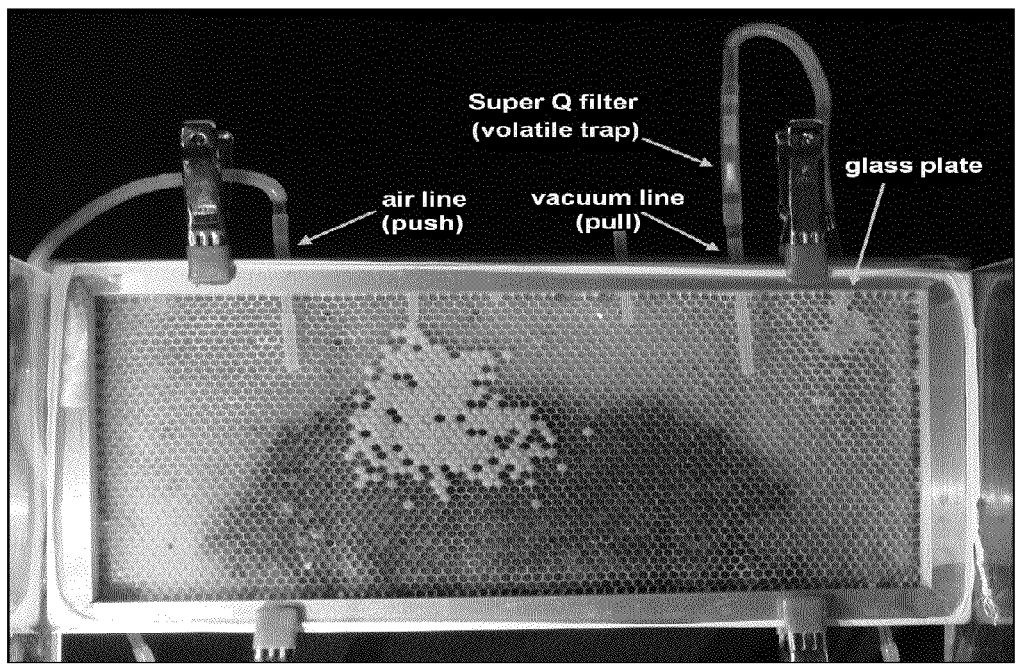
FIG. 2 shows a setup which allowed the capture of volatiles emanating from the comb without capturing frame volatiles as described below; the amount of air escape was minimized and activity on the frame was observed during collections.

Once we demonstrated that volatiles collected from capping bee brood ($5^{th}$ instar) were attractive to *Varroa* mites, the next step was to identify the chemical components of the attractive odors. We collected volatiles from hive materials and bees of different ages and castes to identify volatiles specifically associated with attractive larval hosts. Specific age cohorts of bee larvae and pupae were obtained by the previously described queen caging methods. In order to collect honey bee volatiles from active bees in a comb environment, we enclosed the active brood comb within an observation frame consisting of a glass-covered aluminum frame sunk into the wax between the comb and the wooden frame (FIG. 2).

Figure 3:
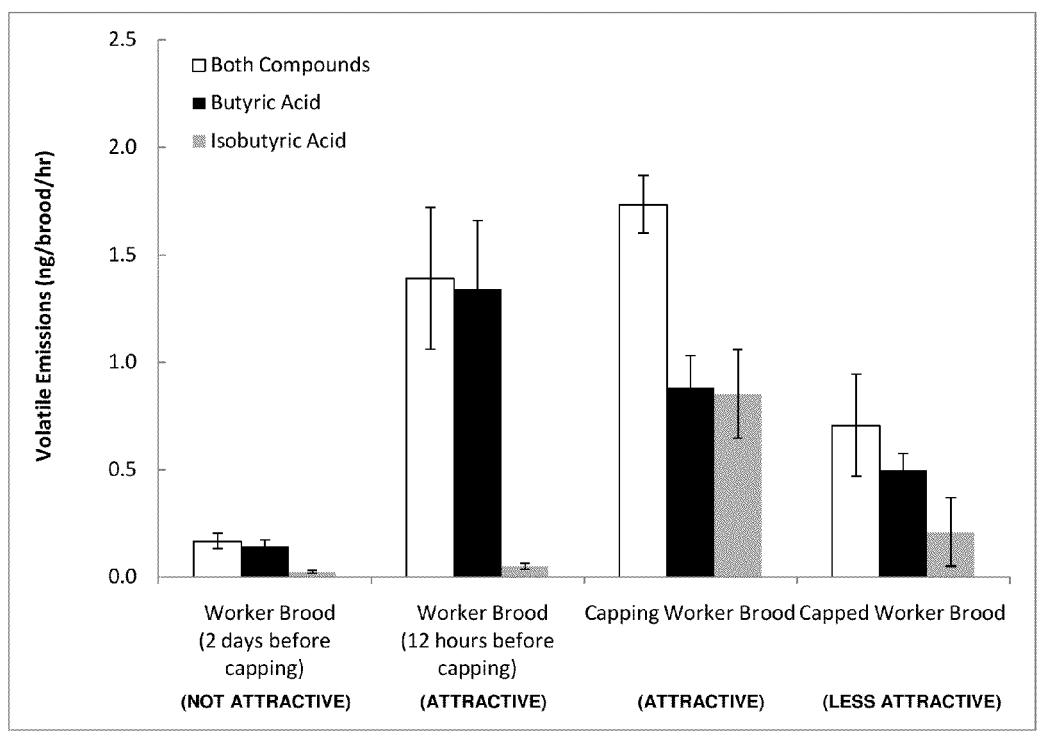
FIG. 3 shows the amount of butyric acid and isobutyric acid given off by bee worker brood of different developmental stages as described below; the increases in acid emissions mirrored the movement into capping and decrease after capping.
Figure 4:
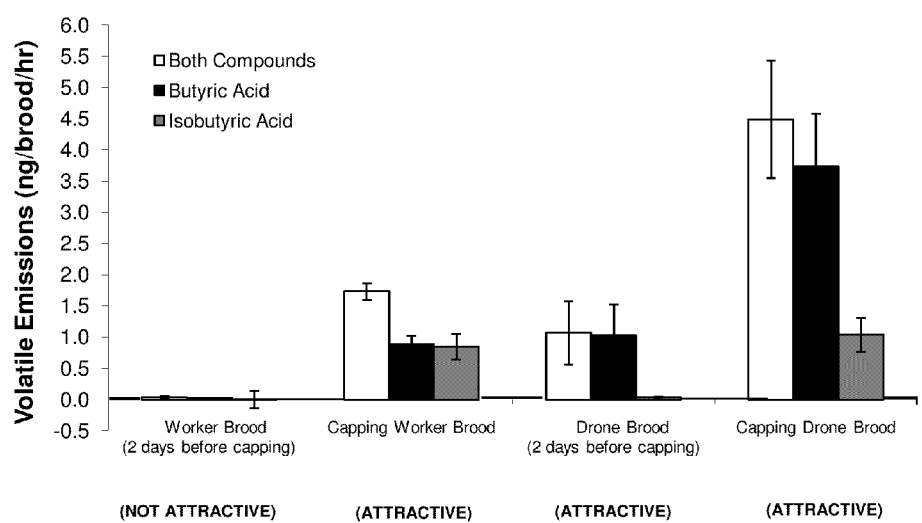
FIG. 4 shows that amounts of butyric acid and isobutyric acid were higher in volatiles released by drone brood than they were in volatiles released by worker brood, thus drone brood was more attractive to *Varroa* mites than worker brood as described below.

Bees were maintained under bee colony environmental conditions by gently pumping clean charcoal-filtered, humidified (~70% relative humidity), warm (93° F.) air into the glass enclosure with a push-pull air flow system. Volatiles were captured by passing the air outflow of the vacuum line through a filter filled with Super Q absorbance adsorbant material (Alltech, Nicholasville, KY; Loughrin, J. H., et al., J. Chem. Ecol., 21: 1217-1226 (1995). For each sample volatiles were collected for three hours. Trapped volatiles were recovered from the SuperQ filters by passing dichloromethane through the packing material, then identified by gas chromatography-mass spectrometry analysis and quantified by gas chromatography flame ionization detection. Butyric acid and isobutyric acid were the two volatiles most consistently associated with larval castes and ages specifically targeted by *Varroa* mites. These two volatiles were released at much higher rates from attractive brood castes and ages than less attractive brood castes and ages. In worker broods, emissions of both volatiles peak as larvae approached the cell capping phase (FIG. 3). Likewise, both volatiles were released near capping at much higher rates by highly attractive drone brood than less attractive worker brood (FIG. 4).

Experiment 3

Figure 5:
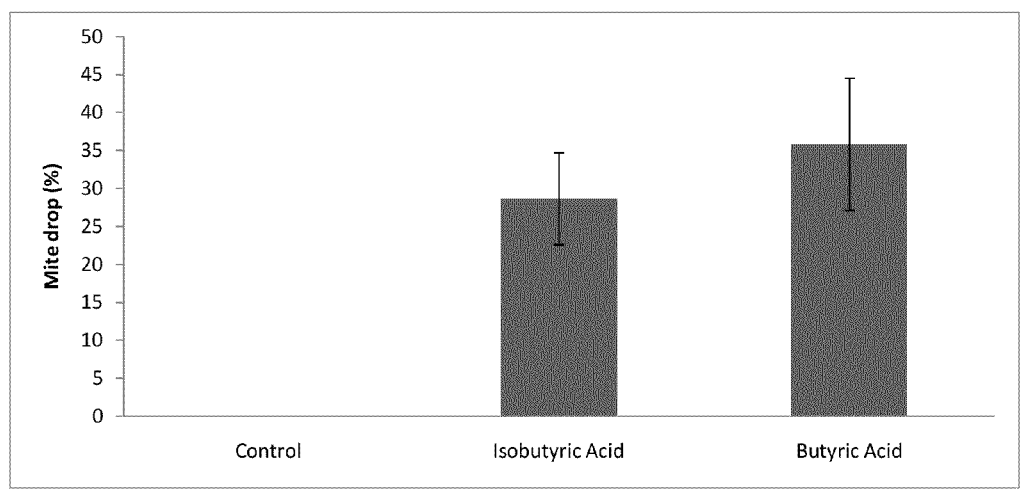
FIG. 5 shows the results of exposing approximately 200 bees per jar to butyric acid isobutyric acid and controls as described below; each treatment was repeated three times and the percent of mites removed from bees is shown.

We then performed a bottom screen assay to assess the response of phoretic mites on adult bees to the acid volatiles. We placed 200 mite-infested adult worker bees in a screen bottomed jar inverted over a water trap. A total of nine jars were used, three replicates of each treatment. The mites and bees were exposed to either butyric acid, isobutyric acid, or a control solvent (methylene chloride) (100 µL) for 20 minutes. Mites that moved off the bees fell into the water trap below. At the end of the experiment, the bees were washed with alcohol to estimate the number of mites that remained on the bees. Surprisingly, significantly more mites fell off bees that were exposed to the acid volatiles than the bees in control jars (FIG. 5). Mites exposed to the acid volatiles surprisingly displayed much higher activity levels than mites in control treatments.

Experiment 4

Figure 6:
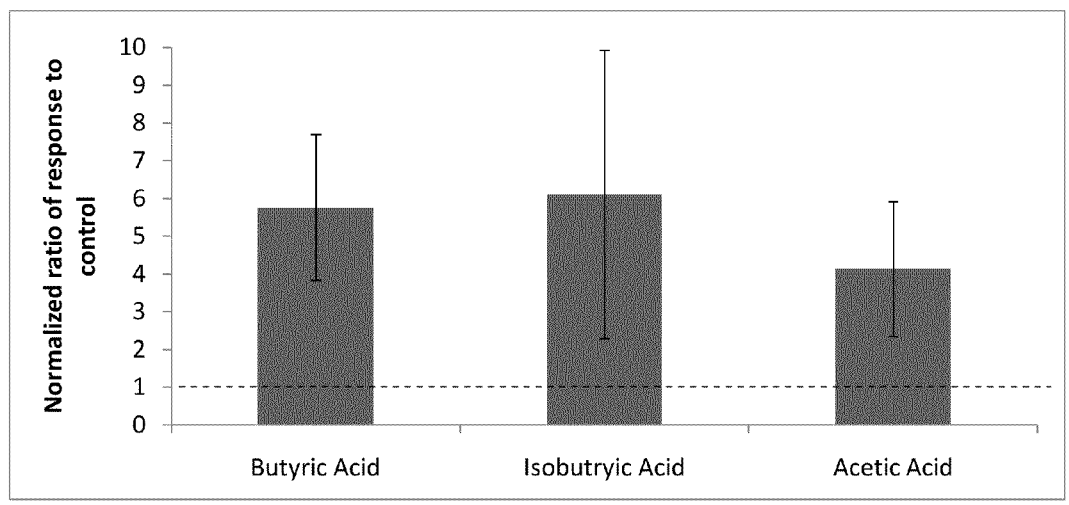
FIG. 6 shows *Varroa* mite response to larval bee related compounds as described below. Each compound was diluted to five percent by volume with methylene chloride and 10 µL was applied to a piece of filter paper, the resultant odors were puffed over a preparation of two *Varroa* mite forelegs spanning an electrode. The responses are the changes in voltage due to nervous response. The responses were normalized in comparison to control puffs.

To determine if mites can detect the acid compounds we used coupled gas chromatography and electroantennographic detection (GC-EAD) and electroantennography (EAG). These methods are generally used with insect antennae but since mites use their forelegs for chemoreception we substituted forelegs for antennae; in terms of the terminology for the methods used we are going to keep with the standard terms containing antennae. A detecting electrode was set up with electrode gel on each contact and then a mite was dissected so that both of its forelegs could be set across the electrodes. The electrode gel provides both a better contact and keeps the forelegs from drying out. For GC-EAD we used a standard containing our two attractive acids along with other short chain acids (i.e., acetic acid, propanoic acid, and hexanoic acid) and common bee odors (iso-pentyl acetate, delta-3-carene, E-(β)-ocimine) at equal concentrations. The GC-EAD surprisingly showed that mites could clearly detect acetic acid, and were also excited by butyric acid and isobutyric acids, while the longer chain acids (propanoic and hexanoic acid) and other bee compounds (iso-pentyl acetate, delta-3-carene, E-(β)-ocimine) did not appear to be detected. We used EAG to determine the responses of forelegs to the individual detected compounds. The mites forelegs clearly responded to all three chemicals that were detected in with GC-EAD (FIG. 6). The dashed line in FIG. 6 represents the level of the control response.

Experiment 5

Figure 7:
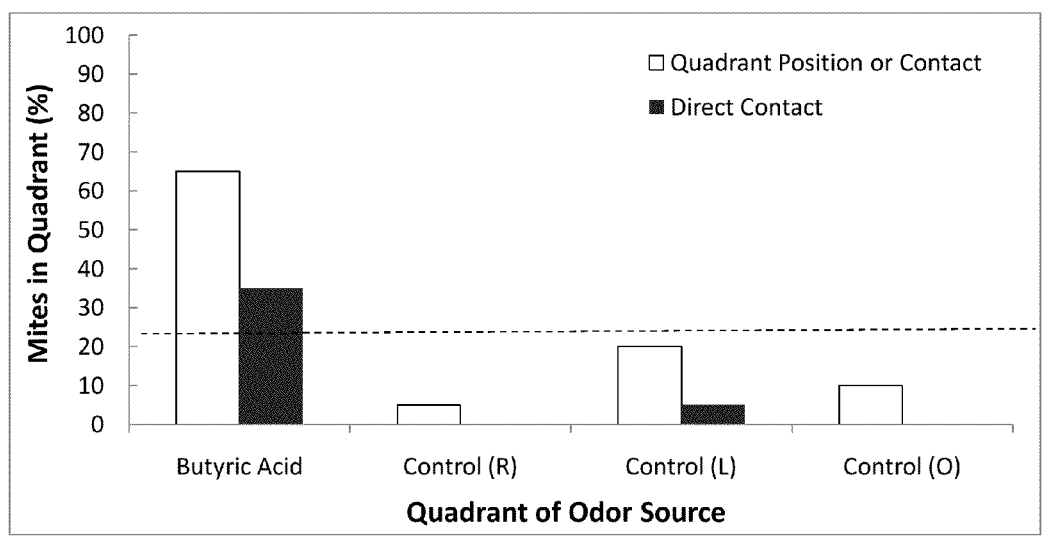
FIG. 7 shows mite attraction to synthetic butyric acid in a four choice arena as described below; mites were introduced into the center of the arena and their location was recorded at the end of five minutes, if they directly passed over the odor source that contact was also recorded.
Figure 8:
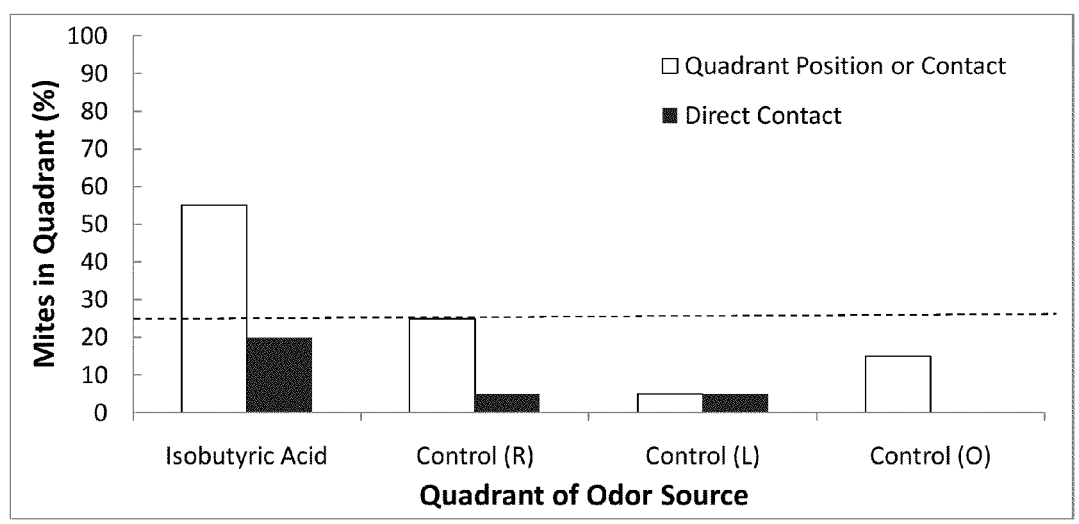
FIG. 8 shows mite attraction to synthetic isobutyric acid in a four choice arena as described below; mites were introduced into the center of the arena and their location was recorded at the end of five minutes, if they directly passed over the odor source that contact was also recorded.
Figure 9:
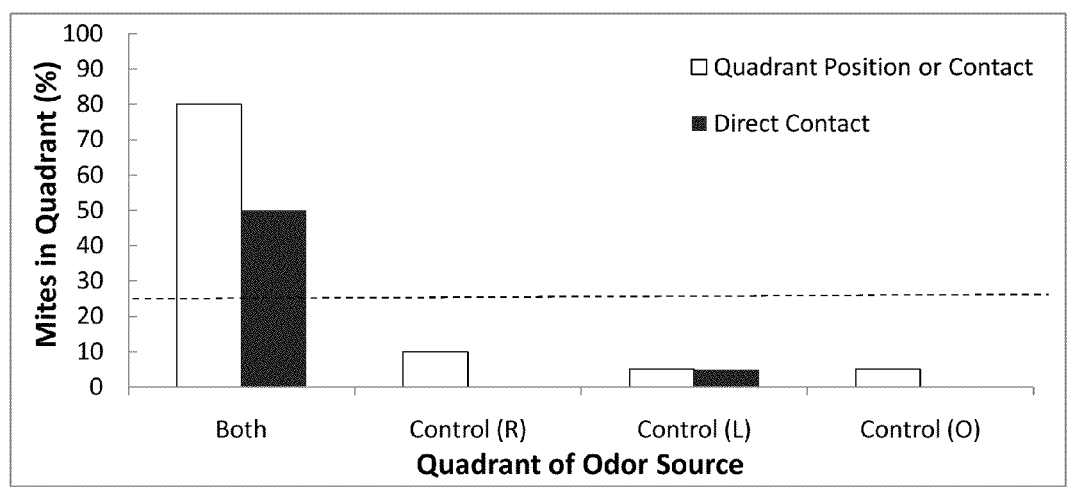
FIG. 9 shows mite attraction to a 1:1 mixture of isobutyric and butyric acid in a four choice arena as described below; mites were introduced into the center of the arena and their location was recorded at the end of five minutes, if they directly passed over the odor source that contact was also recorded.

Once we determined that the mites could perceive and respond to the acid volatiles, we examined whether these acids acted as attractants or repellents. We developed a four choice bioassay to evaluate the responses of mites to highly concentrated volatiles released at very close distances (7 mm). Our choice arena consisted of four odor sources presented directly beneath a permeable mesh floor. Each odor source was introduced by capillary release from a capillary tube, the volatiles diffused up through the permeable mesh floor. Free-roaming (off the adult bee) mites were introduced onto a vertical pin placed in the center of the arena. Mite attraction to a given odor source was scored as direct contact with the odor source or the position at the end of the bioassay (5 minutes). The responses of the mites to the chemicals (FIGS. 7-9) surprisingly showed that the mites were significantly more likely to move in the direction of the brood-related compounds (butyric acid and isobutyric acid), hereafter referred to as attractants; the odor sources were either distilled water only or distilled water with 5% by volume added chemical, there were three controls and one experimental in each bioassay array so each trial had 3 sections with just water and one section with the test acid. The expected value for response is 25% as indicated by the dashed line. However, the mites did not display any arrestant (stopping) behavior, but kept moving in an excited manner. Free-roaming mites were also exposed to these chemicals under the microscope to visually evaluate mite detection, attraction, and arrestant responses to the acid volatiles. Mites surprisingly showed excitation and search behaviors (questing and casting behaviors) when exposed to acid volatiles from capillary tubes. Free-roaming mites surprisingly also moved toward and occasionally into acid droplets, but did not show arrestant behaviors in their presence; later EthoVision bioassays (diffusion bioassays) clearly showed that sustained exposure to high concentrations of butyric acid volatiles also caused arrestant behaviors in mites.

Experiment 6

Figure 10:
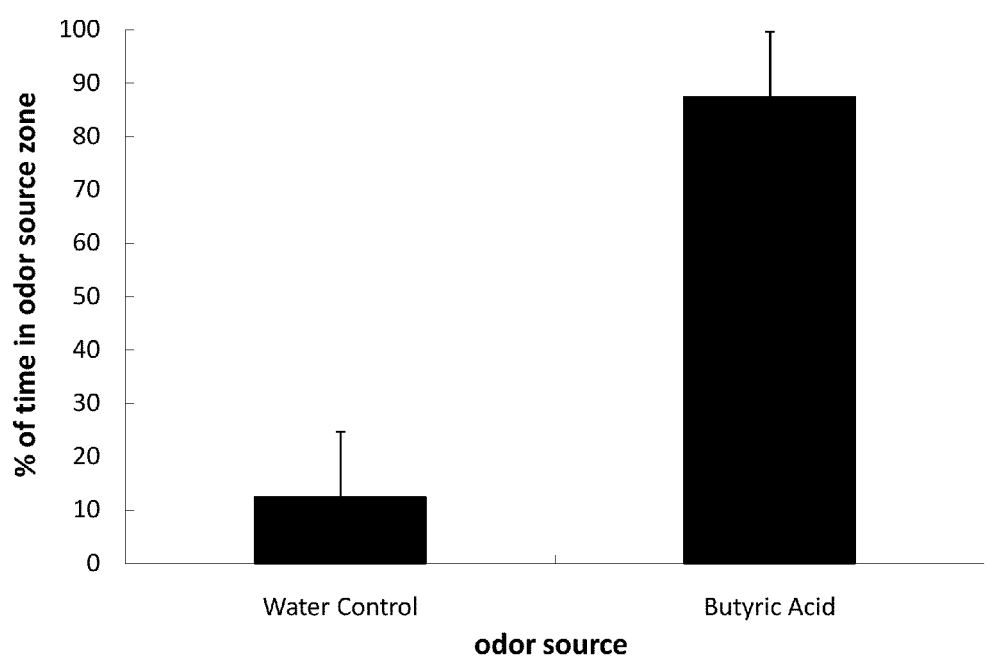
FIG. 10 shows mite attraction to butyric acid in two choice diffusion bioassay, as assessed by ethovision, as described below. Time spent in area over odor sources is clearly significantly different and more time is spent in the area above the Butyric Acid (CA).
Figure 11:
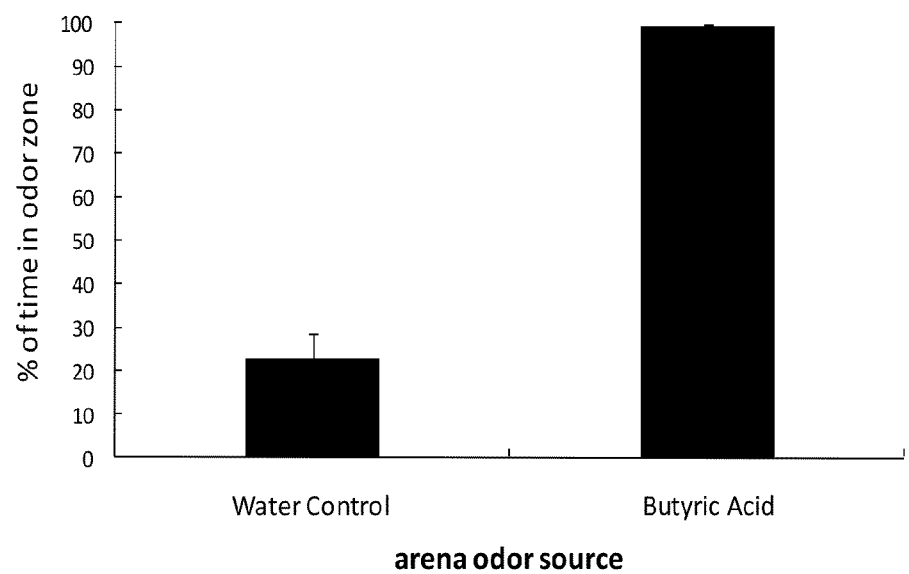
FIG. 11 shows mite response to butyric acid in a no choice test with ethovision analysis as described below. The mites spend significantly more time in the zone over the butyric acid, p<0.001 by t-test. Other analyses show that mites spend significantly less time moving when exposed to the acid as opposed to the water control.

This experiment used the tracking software Ethovision XT (Noldus Information Technology, Leesburg Va.) to monitor the position of mites in an arena. The arena was a four quadrant petri dish 7.5 cm in diameter, the sides of the dish were ground down so that the separations were all the same height as the edges. A plexiglass ring, 7.5 cm outside diameter 2.5 cm high, with 11 micron Nitex fabric attached to the bottom contained the mite and separated the mite from the odor sources but allowed the odors to diffuse through the fabric. The petri dish quadrants were filled either with 5% butyric acid in water, or water only as a control. Opposite quadrants were filled with the same material so that the bottom of each quadrant was completely covered with liquid. This ensured equal surface areas for diffusion of the solute and solvent. Each experiment was conducted with 8 mites. Mites surprisingly spent significantly more time ($p<0.001$) in the zones with the acids than they did in the control zones (FIG. 10). A second set of no choice assays was also performed, these assays used an un-separated petri dish to hold the 5% acid solution and the movements of the mites over the solution were monitored. Mites surprisingly spent more time in the arena $p<0.001$ moving slower and stopping more often when exposed to the acids than when over water (FIG. 11). These results show that the acids surprisingly cause mites to stop in areas where butyric and iso-butyric acid are located and to move towards those areas.

Use of these new naturally produced chemicals to trap or otherwise control *Varroa* mites will significantly reduce the need to use chemical pesticides. Additionally, use of the natural products will result in production of safer consumable products (honey), reduce costs associated with mite control because the chemicals are readily available and inexpensive, reduce exposure of workers to toxicants, and improve honeybee pollination efficacy because the mite load will be reduced.

All of the references cited herein, including U.S. patents, are incorporated by reference in their entirety. Also incorporated by reference in their entirety are the following U.S. Pat. Nos. 7,597,912; 7,544,706; 7,423,068; 6,843,985; 6,342,499; 6,277,371; 6,204,283; 6,037,374; 5,312,622; 5,230,894; 5,227,162; 5,135,758; 5,023,359; 4,876,265; 4,867,731; 4,299,816.

Thus, in view of the above, the present invention concerns (in part) the following:

A method for attracting honey bee parasitic mites to an object or area, comprising (or consisting essentially of or consisting of) treating the object or area with a composition containing a honey bee parasitic mites attracting effective amount of at least one compound selected from the group consisting of butyric acid, isobutyric acid, and mixtures thereof, and optionally a carrier or carrier material. The above method, wherein said honey bee parasitic mites attracting effective amount is more than 0.1% as a solution in a solvent such as but not limited to water and up to pure "neat" material dispensed from a slow release formulation.

The above method, wherein said compound is butyric acid. The above method, wherein said compound is not butyric acid.

The above method, wherein said compound is isobutyric acid. The above method, wherein said compound is not isobutyric acid.

The above method, wherein said compound is not propanoic acid, hexanoic acid, so-pentyl acetate, delta-3-carene, or E-(β)-ocimine.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for attracting honey bee parasitic mites to an object or area, comprising treating the object or area with a composition containing a honey bee parasitic mites attracting effective amount of at least one compound selected from the group consisting of butyric acid, isobutyric acid, and mixtures thereof, and optionally a carrier or carrier material.

2. The method according to claim 1, wherein said compound is butyric acid.

3. The method according to claim 1, wherein said compound is isobutyric acid.

\* \* \* \* \*